United States Patent [19]

Parker et al.

[11] Patent Number: 4,751,220
[45] Date of Patent: Jun. 14, 1988

[54] CRYSTALLINE SALTS OF [3S(Z)]-2[[[1-(2-AMINO-4-THIAZOLYL)-2-[[2,2-DIMETHYL-4-OXO-1-(SULFOOXY)-3-AZETIDINYL]AMINO]-2-OXOETHYLIDENE]-AMINO]OXY]ACETIC ACID

[75] Inventors: W. Lawrence Parker, Pennington; Edward M. Cohen, West Windsor Township, Mercer County; William H. Koster, Pennington, all of N.J.

[73] Assignee: E. R. Squibb & Sons, Inc., Princeton, N.J.

[21] Appl. No.: 944,283

[22] Filed: Dec. 19, 1986

[51] Int. Cl.[4] ............... C07D 403/12; A61K 31/425; A61K 31/71; C07H 17/08
[52] U.S. Cl. ..................................... 514/29; 514/210; 536/7.2; 544/355
[58] Field of Search ................. 514/210, 29; 544/355; 536/7.2

[56] References Cited

U.S. PATENT DOCUMENTS 4,337,197  6/1982  Gordon et al. ............... 540/355
4,533,660  8/1985  Gordon et al. ............... 540/355
4,638,061  1/1987  Slusarchyk .................... 540/355

OTHER PUBLICATIONS

Floyd et al., "Journal of Organic Chemistry", 47:5160 (1982).
Slusarchyk et al., "Heterocycles", 21:191 (1984).
Tanaka et al., paper #854 presented at XXVI Intersci- ence Conference on Antimicrobial Agents and Chemotherapy, Sep. 28, 1986.

Primary Examiner—Mark L. Berch
Attorney, Agent, or Firm—Lawrence S. Levinson; Theodore R. Furman, Jr.

[57] ABSTRACT

In accordance with the present invention an orally active monosulfactam antibiotics having a crystalline structure and thereby improved stability are disclosed. The antibiotics comprise the dierythromycin ($M^\oplus = erythromycin.H^\oplus$) salt or the dicholine ($M^\oplus = HOCH_2CH_2N^\oplus(CH_3)_3$) salt of the acid ($M^\oplus = H^\oplus$) having the formula

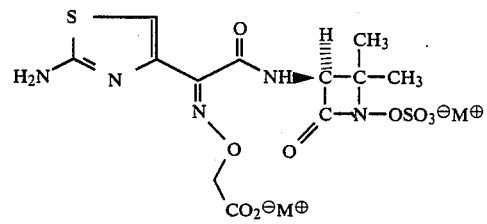

that is, [3S(Z)]-2[[[1-(2-amino-4-thiazolyl)-2-[[2,2-dimethyl-4-oxo-1-(sulfooxy)-3-azetidinyl]-amino]-2-oxoethylidene]amino]oxy]acetic acid.

3 Claims, No Drawings

CRYSTALLINE SALTS OF [3S(Z)]-2[[[1-(2-AMINO-4-THIAZOLYL)-2-[[2,2-DIMETHYL-4-OXO-1-(SULFOOXY)-3-AZETIDINYL]AMINO]-2-OXOETHYLIDENE]-AMINO]OXY]ACETIC ACID

FIELD OF THE INVENTION

This invention relates to improved monosulfactam antibiotics and more particularly concerns the dierythromycin and dicholine salts of [3S(Z)]-2[[[1-(2-amino-4-thiazolyl)-2-[2,2-dimethyl-4-oxo-1-(sulfooxy)-3-azetidinyl]-amino]-2-oxoethylidene]amino]oxy]acetic acid.

BACKGROUND OF THE INVENTION

Gordon et al. in U.S. Pat. No. 533,660 disclose a novel family of β-lactam antibiotics. The preferred oral antibiotics disclosed by Gordon et al. comprise the β-lactam nucleus biologically activated by a sulfate ($-O-SO_3^{\ominus}M^{\oplus}$) substituent attached to the nitrogen atom of the nucleus, and an acylamino substituent in the 3-position as shown in the formula

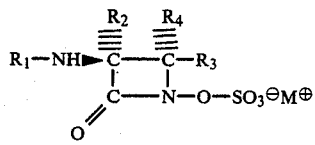

One such compound having the formula

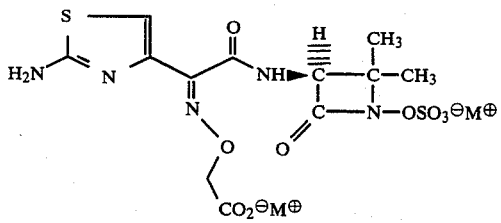

that is, [3S(Z)]-2[[[1-(2-amino-4-thiazolyl)-2-[[2,2-dimethyl-4-oxo-1-(sulfooxy)-3-azetidinyl]-amino]-2-oxoethylidene]amino]oxy]acetic acid ($M^{\oplus}=H^{\oplus}$), is further described in a copending application Ser. No. 695,775, filed Jan. 28, 1985, now U.S. Pat. No. 4,638,061. In the copending application pharmaceutically acceptable salts of that specific monosulfactam, e.g. ammonium salts, alkali metal salts such as sodium and potassium salts, alkaline earth metal salts such as calcium and magnesium salts, and salts derived from organic bases such as dicyclohexylamine, benzathine, hydrabamine, and N-methyl-D-glucamine are disclosed. Many of these salts that are desirable as medicinal agents are generally amorphous in their structure.

While the above compounds are very useful in that they have good activity against gram-negative bacteria, additional stable compounds having an even broader range of antibacterial activity have been sought.

SUMMARY OF THE INVENTION

In accordance with the present invention orally active monosulfactam antibiotics having a crystalline structure and thereby improved stability are disclosed. The antibiotics comprise the dierythromycin salt ($M^{\oplus}=$erythromycin.$H^{\oplus}$) or the dicholine salt ($M^{\oplus}=HOCH_2CH_2N^{\oplus}(CH_3)_3$) of the acid ($M^{\oplus}=H^{\oplus}$) having the formula

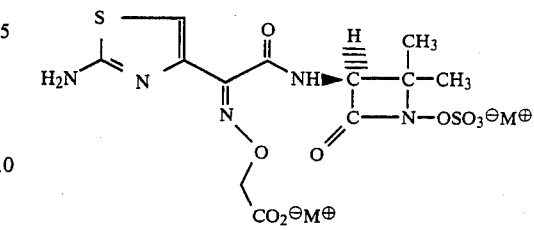

that is, [3S(Z)]-2[[[1-(2-amino-4-thiazolyl)-2-[2,2-dimethyl-4-oxo-1-(sulfooxy)-3-azetidinyl]-amino]-2-oxoethylidene]aminooxy]acetic acid.

DETAILED DESCRIPTION OF THE INVENTION

The orally active monosulfactam antibiotics of the present invention, comprising the dierythromycin ($M^{\oplus}=$erythromycin.$H^{\oplus}$) or dicholine ($M^{\oplus}=HOCH_2CH_2N^{\oplus}(CH_3)_3$) salts of the acid ($M^{\oplus}=H^{\oplus}$) of formula I, are characterized by a distinct crystalline structure. The crystalline structure imparts good chemical stability to these compounds. These salts also have good activity against a wide range of gram-negative bacteria. Additionally, the dierythromycin salt possesses good activity against gram-positive bacteria. These and other qualities make the present antibiotics extremely useful medicinal agents.

Although the prior art has described generally the pharmaceutically acceptable salts of the acid ($M^{\oplus}=H^{\oplus}$) of formula I, the dierythromycin and dicholine salts thereof have not been heretofore disclosed. It is believed that those salts having a distinct crystalline structure will exhibit the highest degree of solid state chemical stability. Therefore, since most of the pharmaceutically acceptable salts of the acid ($M^{\oplus}=H^{\oplus}$) of formula I described in the prior art have been amorphous in their structure, it was unexpected that combining erythromycin or choline hydroxide with the acid ($M^{\oplus}=H^{\oplus}$) of formula I would produce this stable crystalline structure. In fact, the monoerythromycin, monoerythromycinmonosodium and monocholine salts of the acid ($M^{\oplus}=H^{\oplus}$) of formula I were all amorphous. Surprisingly, the dierythromycin salt and the dicholine salt have a distinct crystalline structure providing the compounds with enhanced stability, in addition to their broad antimicrobial spectrum.

To prepare the novel salt of the present invention first the free acid of formula I ($M^{\oplus}=H^{\oplus}$) may be prepared as described in the copending application Ser. No. 695,775, filed Jan. 28, 1985, now U.S. Pat. No. 4,618,061. The acid ($M^{\oplus}=H^{\oplus}$) of formula I is thereafter treated with erythromycin or choline hydroxide to form the antibiotics of the present invention, i.e. the dierythromycin salt ($M^{\oplus}=$erythromycin.$H^{\oplus}$) or the dicholine salt ($M^{\oplus}=HOCH_2CH_2N^{\oplus}(CH_3)_3$) of the acid ($M^{\oplus}=H^{\oplus}$) of formula I.

Alternatively, the starting material can be a salt of the acid ($M^{\oplus}=H^{\oplus}$) of formula I as prepared by the procedures described in U.S. Pat. Nos. 4,533,660, or 4,337,197 or the above-cited pending application Ser. No. 695,775, filed Jan. 28, 1985, now U.S. Pat. No. 4,618,061 or one or the other of the salts of the present invention. The cationic portion of the salt can be removed by known methods, such as treatment with a strong cation exchange resin, to form the acid (M⊕=H⊕) of formula I, which is then combined with erythromycin or choline hydroxide to form the desired product.

For combating a broad spectrum of bacterial infections in mammals, a compound of this invention can be administered to a mammal in need thereof in an amount. of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository. The dicholine salt is effective against gram-negative bacteria and the dierythromycin salt is effective against gram-negative and gram-positive bacteria.

While the dierythromycin and dicholine salts of the acid (M⊕=H⊕) of formula I are preferably employed as crystalline compounds, the amorphous forms of these salts are also novel effective antibacterial agents. As such, the amorphous dierythromycin and dicholine salts are also considered within the scope of the present invention.

The following Example serves to further describe specific embodiments of the novel antibiotics; however, the present invention should not be limited by the details described therein.

EXAMPLE 1

[3S(Z)]-[[[1-(2-AMINO-4-THIAZOLYL)-2-[[2,2-DIMETHYL-4-OXO-1-(SULFOOXY)-3-AZETIDINYL]-AMINO]-2-OXOE-THYLIDENEAMINO]AMINO]-OXY]ACETIC ACID, DICHOLINE SALT

A. [3S(Z)]-[[[1-(2-Amino-4-Thiazolyl)-2-[[2,2-Dimethyl-4-Oxo-1-(Sulfooxy)-3-Azetidinyl]-Amino]-2-Oxoethylidene]-Amino]Oxy]Acetic Acid The title A compound was prepared as described in the copending application Ser. No. 695,775 filed Jan. 28, 1985, now U.S. Pat. No. 4,618,061.

B. [3S(Z)]-[[[1-(2-Amino-4-Thiazolyl)-2-[[2,2-Dimethyl-4-Oxo-1-(Sulfooxy)-3-Azetidinyl]-Amino]-2-Oxoethylidene]Amino]-Oxy]Acetic Acid, Dicholine Salt To a filtered solution of the free acid of part A (7.60 g; 13.7 mmoles) in 200 ml of ethanol was added an absolute ethanol solution of choline hydroxide (53 ml of a 0.465M solution, 24.6 mmol, 90 percent of theoretical amount required) dropwise over 6 minutes. To the resulting solution, which was a pale yellow and slightly cloudy, was added with good stirring isopropanol (250 ml) over 8 minutes and the resulting solution was seeded. After stirring for 20 minutes, isopropanol (82 ml) was added over 10 minutes. After stirring for an additional 25 minutes, the mixture was cooled in an ice bath. After stirring for 20 minutes, isopropanol (82 ml) was added over 10 minutes. After stirring for an additional 15 minutes, isopropanol (82 ml) was added over 10 minutes. After stirring for an additional 20 minutes, isopropanol (82 ml) was added over 10 minutes. After stirring for an additional one hour at 0° C., the mixture was filtered under nitrogen, washed with two 50 ml portions of isopropanol and dried under vacuum to give 7.08 g of the title compound. Crystallinity was confirmed by x-ray diffraction.

EXAMPLE 2

[3S(Z)]-2[[[1-(2-AMINO-4-THIAZOLYL)-2-[[2,2-DIMETHY:-4-OXO-1-(SULFOOXY)-3-AZETIDINYL]-AMINO]-2-OXOETHYLIDENE]-AMINO]OXY]ACETIC ACID, DIERYTHROMYCIN SALT

A. [3S(Z)-2[[[1-(2-Amino-4-Thiazolyl)-2-[[2,2-Dimethyl-4-Oxo-1 -(Sulfooxy)-3-Azetidinyl]-Amino-2-Oxoethylidene]-Amino]Oxy]Acetic Acid, Dicholine Salt The dicholine salt was prepared as described in Example 1.

B. [3S(Z)]-2[[[1-(2-Amino-4-Thiazolyl)-2-[[2,2-Dimethyl-4-Oxo-1-(Sulfooxy)-Azetidinyl]-Amino]-2-Oxoethylidene]-Amino]Oxy]Acetic Acid A solution of the dicholine salt of part A (250 mg; 0.383 mmoles) in 2.5 ml of water was applied to a 2 ml column of Dowex 50W-X2(H+), 200 to 400 mesh, and the column was eluted until the effluent was neutral at which point the effluent contained the title B compound.

C. [3S(Z)]-2[[[1-(2-Amino-4-Thiazolyl)-2-[[2,2-Dimethyl-4-Oxo-1-(Sulfooxy)-Azetidinyl]-Amino]-2-Oxoethylidene-Amino]Oxy]Acetic Acid, Dierythromycin Salt To a solution of erythromycin monohydrate (575 mg; 0.765 mmoles) in 5 ml of methanol was added 8.4 ml of the effluent obtained in part B with agitation. The resulting clear solution was concentrated in vacuo to remove the methanol, giving 5.6 g of a thick aqueous paste. This was washed by centrifugation with one 10-ml and two 5-ml portions of water and dried to constant weight in vacuo at room temperature, giving 369 mg of solid. Equilibration with ambient moisture for 36 hours gave 393 mg of the title compound as a solid. Crystallinity was confirmed by X-ray powder diffraction.

What is claimed is:

1. The dierythromycin and dicholine salts of the compound [3S(Z)]-2[[[1-(2-amino-4-thiazolyl)-2-[[2,2-dimethyl-4-oxo-1-(sulfooxy)-3-azetidinyl]-amino]-2-oxoethylidene]amino]oxy]acetic acid.

2. A compound of claim 1 in crystalline form.

3. A method for treating bacterial infections in mammals which comprises administering to a mammal in need thereof an effective amount of the dierythromycin or dicholine salt of the compound [3S(Z)]-2[[[1-(2-amino-4-thiazolyl)-2-[[2,2-dimethyl-4-oxo-1-(sulfooxy)-3-azetidinyl]-amino]-2-oxoethylidene]amino]oxy]acetic acid.

* * * * *

UNITED STATES PATENT AND TRADEMARK OFFICE
CERTIFICATE OF CORRECTION

PATENT NO. : 4,751,220

DATED : June 14, 1988

INVENTOR(S) : Parker et al.

It is certified that error appears in the above-identified patent and that said Letters Patent is hereby corrected as shown below:

Column 1, line 18, "533,660" should be --4,533,660--;

Column 1, line 21, "$SO_3^{63}$" should be --$SO_3^{\ominus}$--;

Column 1, line 68, "erythromycin.$H^{61}$" should be --erythromycin·$H^{\oplus}$--;

Column 2, line 14, "[2,2-" should be --[[2,2- --;

Column 2, line 16, "aminooxy]" should be --amino]oxy]--;

Column 2, line 22, "erythromycin.$H^{\oplus}$" should be --erythromycin·$H^{\oplus}$--;

Column 2, line 55, "4,618,061" should be --4,638,061--;

Column 2, line 58, "erythromycin.$H^{\oplus}$" should be --erythromycin·$H^{\oplus}$--;

Column 2, line 65, "4,618,061" should be --4,638,061--;

Column 3, line 34, "THYLIDENEAMINO]AMINO]" should be --THYLIDENE]AMINO]--;

Column 3, line 41, "4,618,061" should be --4,638,061--;

Column 4, line 11, "Dimethy:" should be --dimethyl--;

Column 4, line 15, "[3S(Z)" should be --[3S(Z)]--;

Column 4, line 22, --3-- should be inserted between "(Sulfooxy)-" and "Azetidinyl]";

UNITED STATES PATENT AND TRADEMARK OFFICE
CERTIFICATE OF CORRECTION

PATENT NO. : 4,751,220

DATED : June 14, 1988

INVENTOR(S) : Parker et al.

It is certified that error appears in the above-identified patent and that said Letters Patent is hereby corrected as shown below:

Column 4, line 30, --3-- should be inserted between "(Sulfooxy)-" and "Azetidinyl]";

IN THE ABSTRACT:

Lines 4 and 5, "erythromycin.H$^{\oplus}$)" should be --erythromycin·H$^{\oplus}$)--.

Signed and Sealed this

Fifteenth Day of November, 1988

Attest:

DONALD J. QUIGG

*Attesting Officer*  *Commissioner of Patents and Trademarks*